United States Patent
Lee et al.

(10) Patent No.: US 8,808,761 B2
(45) Date of Patent: Aug. 19, 2014

(54) COMPOSITION OF SKIN EXTERNAL APPLICATION CONTAINING ROSE EXTRACT AND EPIGALLOCATECHIN GALLATE(EGCG)

(75) Inventors: Hwa Jun Lee, Gyeonggi-do (KR); Jun Cheol Cho, Gyeonggi-do (KR); Sang Hoon Han, Gyeonggi-do (KR)

(73) Assignee: Amorepacific Corporation, Seoul (KR)

( * ) Notice: Subject to any disclaimer, the term of this patent is extended or adjusted under 35 U.S.C. 154(b) by 1315 days.

(21) Appl. No.: 11/795,867

(22) PCT Filed: Nov. 1, 2005

(86) PCT No.: PCT/KR2005/003642
§ 371 (c)(1),
(2), (4) Date: Nov. 20, 2007

(87) PCT Pub. No.: WO2006/083072
PCT Pub. Date: Aug. 10, 2006

(65) Prior Publication Data
US 2008/0160114 A1    Jul. 3, 2008

(30) Foreign Application Priority Data
Feb. 3, 2005 (KR) .................. 10-2005-0009988

(51) Int. Cl.
*A61K 36/00* (2006.01)
*A61K 36/73* (2006.01)
*A61K 36/82* (2006.01)
*A61Q 19/08* (2006.01)
*A61K 8/49* (2006.01)
*A61K 8/97* (2006.01)

(52) U.S. Cl.
CPC ................ *A61K 8/498* (2013.01); *A61Q 19/08* (2013.01); *A61K 8/97* (2013.01)
USPC ............................ 424/729; 424/765; 424/725

(58) Field of Classification Search
None
See application file for complete search history.

(56) References Cited

U.S. PATENT DOCUMENTS

| 5,670,154 A * | 9/1997 | Hara et al. ............... 424/729 |
| 2003/0026818 A1* | 2/2003 | Hoshino et al. ............... 424/401 |
| 2003/0175234 A1* | 9/2003 | Hernandez et al. ............ 424/74 |

FOREIGN PATENT DOCUMENTS

| JP | 03127714 A | * | 5/1991 |
| JP | 1995-309770 | | 11/1995 |
| JP | 2002029959 A | * | 1/2002 |
| KR | 2002062513 A | * | 7/2002 |
| KR | 2004043971 A | * | 5/2004 |
| KR | 10-2005-0011889 | | 1/2005 |
| WO | WO 0000162 | * | 1/2000 |

OTHER PUBLICATIONS

International Search Report mailed Feb. 27, 2006.
Jhou YD et al.: "Hypoxia-inducible factor-1 activation by (-)-epicatechin gallate: potential adverse effects of cancer chemoprevention with high-does green tea extracts." In J Nat Prod 2004 vol. 67, No. 12, pp. 2063-2069.
Tobe SE: "The green tea polyphenol, epigallocatechin-3-gallate, protects against the oxidative cellular and genotoxic damage of UVA radiation," In Int J Cancer 2002, vol. 102, No. 5, pp. 439-444.
Elmets CA et al.: "Cutaneous photoprotection from ultraviolet injury by green tea polyphenols," In J Am Acad Dermatol., 2001, vol. 44, No. 3., pp. 425-432.
Official Action (with English translation) in Chinese patent application 200580047678.4 dated Jun. 5, 2009.
Korean Office Action and English translation in Korean application Serial No. 10-2005-0009988 mailed Jul. 14, 2011.

* cited by examiner

*Primary Examiner* — Qiuwen Mi
(74) *Attorney, Agent, or Firm* — Nixon & Vanderhye P.C.

(57) ABSTRACT

The present invention relates to a composition of skin external application comprising rose extracts and epigallocatechin gallate (EGCG) as effective ingredients, more particularly to a composition of skin external application that contains rose extracts and EGCG, thereby promoting the synthesis of collagen fiber to promote superior skin elasticity and skin wrinkle improvement with long-lasting effect.

4 Claims, No Drawings

COMPOSITION OF SKIN EXTERNAL APPLICATION CONTAINING ROSE EXTRACT AND EPIGALLOCATECHIN GALLATE(EGCG)

This application is the U.S. national phase of International Application No. PCT/KR2005/003642 filed 1 Nov. 2005 which designated the U.S. and claims priority to KR 10-2005-0009988 filed 3 Feb. 2005, the entire contents of each of which are hereby incorporated by reference.

TECHNICAL FIELD

The present invention relates to a composition of skin external application containing EGCG (Epigallocatechin gallate) and rose extracts.

More particularly, the present invention relates to a composition of skin external application containing EGCG (Epigallocatechin gallate) and rose extracts that promotes the collagen biosynthesis and thereby gives superior skin elasticity and skin wrinkle improvement with long-lasting effect.

BACKGROUND ART

Human skin, as a primary protective barrier, protects the vital organs of the body from external irritants such as changes in temperature or humidity, ultraviolet rays and contaminants. However, as skin ages, the secretion of various hormones regulating metastasis is reduced, and the function of immunocytes and the activity of cells are lowered. In addition, due to the increase of UV light and oxygen free radicals resulting from contamination such as ozone layer destruction, physical and chemical stimulus and stress are generated, which promotes skin aging. In order to prevent skin aging and keep more healthy and beautiful skin, studies have been made to keep the inherent function of skin and to activate skin cells, and thereby to effectively inhibit skin aging, by using physiologically active substances obtained from various animals, plants and microorganisms.

It is known that EGCG increases the immunity of the human body, and has a superior antioxidant effect and anti-cancer effect when orally administered. In addition, it is known that, when applied on skin, EGCG promotes synthesis of collagen, which is the constituent of cartilage, capillary vessel and muscle, and destroys chemical substances generated by UV light, thereby preventing skin damage, as well as preventing skin aging, preserving healthy skin, and having superior whitening effects. Therefore, it is expected that EGCG shows excellent effects when applied in cosmetic composition as well as medical composition and home appliances.

However, as EGCG has a chemical structure of polyphenol, and has strong antioxidant effects, it reacts sensitively in external environments such as in air, especially to oxygen, heat and light, thereby being easily decomposed by oxidation.

DISCLOSURE

Technical Solution

The present inventors found that a composition of skin external application comprising EGCG and rose extracts promotes collagen synthesis in the skin derma, thus giving superior skin wrinkle improvement with long-lasting effect, and thereby completed the present invention.

Therefore, the object of the present invention is to provide a composition of skin external application giving superior skin wrinkle improvement with long-lasting effect.

Effect of the Invention

The composition of skin external application comprising EGCG and rose extracts according to the present invention gives superior skin wrinkle improvement with long-lasting effect. Thus, in the present invention, a composition of skin external application giving superior skin wrinkle improvement with long-lasting effects can be provided.

BEST MODE FOR CARRYING OUT THE INVENTION

To attain the above object, the present invention provides a composition of skin external application comprising EGCG and rose extracts.

The EGCG has preferably water-stabilized EGCG capsule formulation, and the rose extracts are preferably the extracts of rose sprout.

The water-stabilized EGCG capsule according to the present invention contains 0.01-30% by weight of pure EGCG, and is prepared by mixing positive polymer, negative polymer or a mixture thereof; water insoluble polymer, amphiphilic polymer or a mixture thereof; and antioxidants.

A process for preparing the water-stabilized EGCG capsule composition used in the present invention comprises steps of: mixing hydrophilic solvent; EGCG; positive polymer, negative polymer or a mixture thereof; antioxidants; and water insoluble polymer, amphiphilic polymer or a mixture thereof, at room temperature; and adding water, hydrophilic solvent or a mixture thereof to the above mixture to prepare a capsule.

Another process for preparing the water-stabilized EGCG capsule composition used in the present invention comprises steps of: mixing hydrophilic solvent; EGCG; and water insoluble polymer, amphiphilic polymer or a mixture thereof, at room temperature;

adding water, hydrophilic solvent or a mixture thereof to the above mixture to dissolve the mixture; and mixing positive polymer, negative polymer or a mixture thereof to the dissolved mixture.

In the above two processes, said EGCG is contained in an amount of 0.01-30 wt %, said positive polymer, negative polymer or the mixture thereof of 0.1-5.0 wt %, said water insoluble polymer, amphiphilic polymer or the mixture thereof of 0.5-25.0 wt %, said antioxidant of 0.1-10 wt % based on the total weight of the capsule, and water and the hydrophilic solvent contained in the balance.

In the present invention, the amount of the water-stabilized EGCG capsule is preferably 0.01-50 wt % based on the total composition. If the amount of the water-stabilized EGCG capsule is below 0.01 wt % based on the total composition, it is hard to expect any effect; and if the amount exceeds 50 wt %, side effects due to overuse are of concern. If the amount of rose sprout extracts is below 0.01 wt % based on the total composition, it is hard to expect any effect; and if the amount exceeds 50 wt %, side effects due to overuse are of concern.

Rose has excellent ingredients in its sprout, leafs, stem and root as well as its fruit, and has been used as therapeutics for a thousand years. In particular, it is known by experiments that the extracts of rose sprout have much vitamin B, C, etc., and thus effectively prevent skin damage due to UV light and antioxidants, and promote skin elasticity.

The extracts of rose sprout used in the present invention are preferably prepared by extracting with butylene glycol the sprout of the wild rose that inhabits an alpine region. These rose sprout extracts have a large quantity of physiologically active substances such as vitamin B and C, and thus have antioxidant effects, and help recovery of the damaged skin to promote its elasticity.

The formulation of the composition of skin external application comprising EGCG and rose extracts according to the present invention is not limited particularly. It may be formulated into skin softeners, nutrient toilet water, nutrient creams, massage creams, packs, gels or skin adhesive type cosmetics. In addition, it may be formulated into trans-dermal type such as lotions, ointments, gels, creams, patches or sprays.

MODE FOR INVENTION

The present invention is described in more detail by way of the following examples. However, these examples are provided for the purpose of illustration only and should not be construed as limiting the scope of the invention, which will be apparent to one skilled in the art.

Reference Example 1

Preparation of Water-Stabilized EGCG Capsule

TABLE 1

| Ingredients | Content (wt %) |
|---|---|
| Glycerin | 10 |
| Acetone | 50 |
| Sugar | 1 |
| Chitosan | 1 |
| Tyrosine | 2 |
| EGCG | 5 |
| Polyester | 10 |
| Water | To 100 |

Water-stabilized EGCG capsule was prepared according to the composition in the above Table 1. The preparation process was as follows:

1) Glycerin and acetone as hydrophilic solvents were put into a flask, and EGCG was added thereto and dissolved.

2) At room temperature, sugar and chitosan as polar polymer and tyrosine as antioxidant were added to the solution of 1) and dissolved.

3) Polyester as water insoluble polymer was dissolved into a mixture of glycerin and acetone as hydrophilic solvents. If desired, the dissolution of water insoluble polymer could be accomplished at increased temperature.

After dissolution, the temperature is decreased to room temperature.

4) The solution of 2) and the water insoluble polymer solution of 3) were mixed.

5) The solution of 4) was added to a mixture of water, and glycerin and acetone as hydrophilic solvent, with slow stirring to prepare capsule.

6) After the completion of capsule preparation, acetone was removed at about 100 mm Hg, 60° C.

Experimental Example 1

Efficacy on the Collagen Biosynthesis of Human Skin Cell

Human fibroblast was cultured in 24-well microplates, and the culture medium thereof was changed to one containing the substances in Table 2. At 3 days of cultivation, 0.5 ml of DMEM culture medium containing 10% FBS was added to each well, then 10 µCi of L [2,3,4,5-3H]-proline was added thereto. 24 hours later, the culture medium and the cells contained in each well were raked, then put into 5% TCA (Trichloroacetic acid) solution. Each sample was then divided into 2 test tubes, and 1 unit/µl of type I collagenase was added to one of each pair of test tubes, and cultured at 37° C. for 90 minutes. The other test tube of each pair was stored at 4° C. 0.05 ml of 50% TCA was then added to every test tube, the test tubes were left at 4° C. for 20 minutes, then each was centrifuged at 12,000 rpm for 10 minutes. Each supernatant and sediment was treated with Liquid Scintillation Counter (LSC) to obtain a CPM (Count Per Minute) value, then the Relative Collagen Biosynthesis value (RCB) of each control and experimental group was obtained based on the below Numerical Formula 1. The results are obtained as relative values, setting the value of the control, which does not contain any of the substances of Table 2, as 100. The results are shown in Table 2.

RCB (%)=(cpm of collagen)/{(cpm of total collagen)×5.4+cpm of collagen)}×100    [Numerical Formula 1]

TABLE 2

| | Concentration (%) | Relative collagen biosynthesis value (RCB) (%) |
|---|---|---|
| Water-stabilized EGCG capsule in Reference Example 1 | 10 | 146 |
| | 1 | 110 |
| Extracts of rose sprout | 10 | 110 |
| | 1 | 102 |
| Control | — | 100 |

As can be seen in the above Table 2, water stabilized EGCG capsule and rose sprout extracts increased collagen biosynthesis of fibroblast in a concentration-dependent manner.

Examples 1-4 and Comparative Examples 1-5

Examples 1-4 and Comparative Examples 1-5 were prepared as cream formulation, according to the composition of Table 3 below. In Table 3, the rose extracts are obtained from leafs, stems and roots of rose.

TABLE 3

| | Contents (wt %) | | | | | | | | |
|---|---|---|---|---|---|---|---|---|---|
| | Formulation Example | | | | Comparative Formulation Example | | | | |
| Materials | 1 | 2 | 3 | 4 | 1 | 2 | 3 | 4 | 5 |
| Distilled water | To 100 | To 100 | To 100 | To 100 | To 100 | To 100 | To 100 | To 100 | To 100 |
| Water stabilized EGCG capsule in Reference | 5.0 | — | 5.0 | — | — | 5.0 | — | — | — |

TABLE 3-continued

|  | Contents (wt %) | | | | | | | | |
|---|---|---|---|---|---|---|---|---|---|
|  | Formulation Example | | | | Comparative Formulation Example | | | | |
| Materials | 1 | 2 | 3 | 4 | 1 | 2 | 3 | 4 | 5 |
| Example 1 |  |  |  |  |  |  |  |  |  |
| Pure EGCG | — | 0.2 | — | 0.2 | — | — | 0.2 | — | — |
| Extracts of rose sprout | 5.0 | 5.0 | — | — | — | — | — | 5.0 | — |
| Rose extracts | — | — | 5.0 | 5.0 | — | — | — | — | 5.0 |
| Vegetable hydrogenated oil | 1.50 | 1.50 | 1.50 | 1.50 | 1.50 | 1.50 | 1.50 | 1.50 | 1.50 |
| Glycerol stearate | 0.60 | 0.60 | 0.60 | 0.60 | 0.60 | 0.60 | 0.60 | 0.60 | 0.60 |
| Cetearyl alcohol | 2.00 | 2.00 | 2.00 | 2.00 | 2.00 | 2.00 | 2.00 | 2.00 | 2.00 |
| Polygrycery-10 penta stearate, Behenyl alcohol and Sodium. | 1.00 | 1.00 | 1.00 | 1.00 | 1.00 | 1.00 | 1.00 | 1.00 | 1.00 |
| Arachidyl behenyl alcohol | 1.00 | 1.00 | 1.00 | 1.00 | 1.00 | 1.00 | 1.00 | 1.00 | 1.00 |
| Cetyl aryl alcohol & cetearyl glucoside | 2.00 | 2.00 | 2.00 | 2.00 | 2.00 | 2.00 | 2.00 | 2.00 | 2.00 |
| PEC-100 stearate, glycerol olate and propylene glycol | 1.50 | 1.50 | 1.50 | 1.50 | 1.50 | 1.50 | 1.50 | 1.50 | 1.50 |
| Caprilic/carlic triglyceride | 11.00 | 11.00 | 11.00 | 11.00 | 11.00 | 11.00 | 11.00 | 11.00 | 11.00 |
| Cyclomethicone | 6.00 | 6.00 | 6.00 | 6.00 | 6.00 | 6.00 | 6.00 | 6.00 | 6.00 |
| Preservative, Perfume, pigment | q.s. | q.s. | q.s. | q.s. | q.s. | q.s. | q.s. | q.s. | q.s. |
| Triethanolamine | 0.10 | 0.10 | 0.10 | 0.10 | 0.10 | 0.10 | 0.10 | 0.10 | 0.10 |

Experimental Example 2

Efficacy on Collagen Biosynthesis of Animal

To confirm the collagen biosynthesis efficacy of the composition, cream formulations examples 1-4 and comparative examples 1-5 were prepared, and were applied on the backs of hairless mice for 1 week from the times of immediately after the preparation, 10 weeks after preparation and 20 weeks after preparation. The mouse was then biopsied and collagen immunohistochemical staining was performed. The results were obtained as relative value, setting the value of the control group as 100. The results are shown in Table 4.

TABLE 4

|  | Collagen Biosynthesis (%) | | |
|---|---|---|---|
|  | Immediately after the preparation | 10 weeks after | 20 weeks after |
| Example 1 | 138 | 138 | 137 |
| Example 2 | 122 | 119 | 116 |
| Example 3 | 119 | 114 | 112 |
| Example 4 | 115 | 112 | 110 |
| Comparative Example 1 (Control) | 100 | 100 | 100 |
| Comparative Example 2 | 112 | 111 | 112 |
| Comparative Example 3 | 110 | 110 | 105 |
| Comparative Example 4 | 105 | 102 | 101 |
| Comparative Example 5 | 101 | 101 | 100 |

As can be seen in the above Table 4, the groups applied with the creams of Examples 1-4 show increased collagen biosynthesis than the group applied with the cream of Comparative Example 1, by 38%, 22%, 19% and 15%. In particular, in the case of Example 1, which used both water-stabilized EGCG capsule and rose sprout extracts, collagen biosynthesis was increased by 38%, and the effect retained after 20 weeks. From this, it can be recognized that, in the present invention, the effect is considerably increased and the effect is long lasting when the mixture of water-stabilized EGCG capsule and rose sprout extracts is used.

Experimental Example 3

Improvement of Skin Elasticity in the Human Body

The following was performed to identify the effects of the above formulations in Table 3 on the improvement of skin elasticity. 90 women aged 30-39 were divided into 3 groups (30 people per group). To each group, the formulation 1 or 2 or comparative formulation 1 was applied twice per day for 12 weeks at 24~26° C., 76% RH. The skin elasticity of skin was determined using cutomer (Cutometer SEM 575, C+K Electronic GmbH, Germany).

The values R8 [R8 (left)-R8 (right)] were obtained, and are shown in Table 5, wherein R8 (left) is the skin elasticity of the control and R8 (right) is the skin elasticity of the estimated group, and thus the value R8 shows the extent of the viscoelasticity. The control is the group untreated with the formulations.

TABLE 5

|  | Skin elasticity effect (R8) |
|---|---|
| Comparative Example 1 | 0.05 |
| Example 1 | 0.38 |
| Example 2 | 0.20 |

As can be seen in Table 5, the group treated with the formulation of Example 1 comprising both water-stabilized EGCG and rose sprout extracts shows superior increase of skin elasticity than the groups treated with the formulations of Example 2 and Comparative Example 1.

Separately, after completion of the experiment, questionnaires were completed by the subjects to determine subjective evaluation of the effect. The results are shown in Table 6.

TABLE 6

|  | Number of the respondents | | | |
| --- | --- | --- | --- | --- |
|  | Very Good | Good | Normal | Insufficient |
| Comparative Example 1 | 1 | 1 | 5 | 3 |
| Example 1 | 1 | 3 | 6 | 0 |
| Example 2 | 3 | 6 | 1 | 0 |

From the above Table 6, it can be confirmed that the skin elasticity is improved when applying the formulation of Example 1 containing water-stabilized EGCG capsule and rose sprout extracts.

Experimental Example 4

Improvement of Skin Wrinkle

The following was performed to identify the effects of the above formulations of Examples 1 and 2, and Comparative Examples 1 and 2 on the improvement of skin wrinkle. 80 women aged 30-39 were divided into 4 groups (20 people per group). To each group, the formulation 1 or 2, or comparative formulation 1 or 2 was applied twice per day for 8 weeks, and replicas were prepared after 8 weeks using silicon. The state of skin wrinkles was image analyzed by visiometer (SV600, Courage+Khazaka Electronic GmbH, Germany). The average of the values obtained by subtracting each parameter value before the application from the same person's corresponding parameter value 8 weeks later are shown in Table 7.

TABLE 7

| Clinical result 8 weeks after using | R1 | R2 | R3 | R4 | R5 |
| --- | --- | --- | --- | --- | --- |
| Example 1 | −0.26 | −0.25 | −0.13 | −0.03 | −0.03 |
| Example 2 | −0.10 | −0.10 | −0.07 | −0.01 | −0.02 |
| Comparative Example 1 | 0.28 | 0.27 | 0.22 | 0.04 | 0.04 |
| Comparative Example 2 | 0.27 | 0.26 | 0.21 | 0.03 | 0.02 |

R1: Difference between the maximum value and the minimum value of skin wrinkle contour
R2: Average of R1 obtained by the difference between the value of an arbitrary contour and the value of the fifth contour from the arbitrary contour
R3: Maximum of R1 obtained by the difference between the value of an arbitrary contour and the value of the fifth contour from the arbitrary contour
R4: Average of each peak-to-peak value at the baseline of wrinkle contour
R5: Difference between the baseline and the value of each wrinkle contour As can be seen in Table 7, Examples 1 and 2 are superior in improvement of skin wrinkle to the Comparative Examples 1 and 2, and especially the effect of Example 1 was excellent.

The invention claimed is:

1. A composition for external application to the skin comprising, as active ingredients, BG (butylene glycol)-extracts of rose sprout and water-solubilized epigallocatechin gallate (EGCG), wherein the water-solubilized epigallocatechin gallate (EGCG) is stabilized against decomposition by oxidation in water by mixing an aqueous solution comprising a water-soluble polymer and a water-insoluble polymer together with a mixture of water, glycerin and acetone.

2. The composition according to claim 1, wherein the water-stabilized EGCG is present in an amount of 0.01 to 50 wt % based on the total weight of the composition.

3. The composition according to claim 1, wherein the BG extracts of rose sprout are present in an amount of 0.01 to 50 wt % based on the total weight of the composition.

4. The composition according to claim 1, wherein the composition is for the improvement of skin wrinkle.

* * * * *